US009775526B2

(12) United States Patent
Ariga et al.

(10) Patent No.: US 9,775,526 B2
(45) Date of Patent: Oct. 3, 2017

(54) BLOOD PRESSURE METER AND PUMP DRIVING SYSTEM

(71) Applicants: Omron Healthcare Co., Ltd., Muko-shi, Kyoto (JP); Murata Manufacturing Co., Ltd., Nagaokakyo-shi, Kyoto-fu (JP)

(72) Inventors: Hiroyasu Ariga, Kyoto (JP); Kenjiro Okaguchi, Nagaokakyo (JP); Toshinari Tabata, Nagaokakyo (JP); Gaku Kamitani, Nagaokakyo (JP)

(73) Assignees: OMRON HEALTHCARE CO., LTD., Kyoto (JP); MURATA MANUFACTURING CO., LTD., Kyoto (JP)

( * ) Notice: Subject to any disclaimer, the term of this patent is extended or adjusted under 35 U.S.C. 154(b) by 400 days.

(21) Appl. No.: 14/516,777

(22) Filed: Oct. 17, 2014

(65) Prior Publication Data
US 2015/0038858 A1 Feb. 5, 2015

Related U.S. Application Data

(63) Continuation of application No. PCT/JP2013/060231, filed on Apr. 3, 2013.

(30) Foreign Application Priority Data

Apr. 19, 2012 (JP) .................................. 2012-095287

(51) Int. Cl.
*A61B 5/021* (2006.01)
*F04B 45/047* (2006.01)
(Continued)

(52) U.S. Cl.
CPC .......... *A61B 5/02141* (2013.01); *A61B 5/024* (2013.01); *A61B 5/0225* (2013.01);
(Continued)

(58) Field of Classification Search
CPC ................ F04B 45/047; F04B 2203/00; F04B 2203/0202
(Continued)

(56) References Cited

U.S. PATENT DOCUMENTS 5,080,218 A * 1/1992 Izume .................. H01L 41/042
198/751
2004/0007941 A1 1/2004 Yuasa et al.
(Continued)

FOREIGN PATENT DOCUMENTS

CN 101960321 A 1/2011
JP 2000-171320 A 6/2000
(Continued)

OTHER PUBLICATIONS

Official Communication issued in corresponding Chinese Patent Application No. 201380020501.X, dated Sep. 25, 2015.
(Continued)

*Primary Examiner* — Charles Freay
*Assistant Examiner* — Kenneth J Hansen
(74) *Attorney, Agent, or Firm* — Keating and Bennett, LLP

(57) ABSTRACT

In the present invention, a pump driving circuit includes a step-up unit that steps up a first DC voltage from a power supply and outputs it as a second DC voltage, and an H bridge unit that has first and second series circuits that each include two switching elements connected in series between a high potential corresponding to the second DC voltage and a reference potential. According to a control signal from the control unit, the two switching elements of the first series circuit and the two switching elements of the second series circuit are switched on and off. A voltage generated between a first contact point between the two switching elements of the first series circuit, and a second contact point between
(Continued)

the two switching elements of the second series circuit is used as a driving voltage for driving a pump.

8 Claims, 12 Drawing Sheets

(51) Int. Cl.
    *A61B 5/0225*     (2006.01)
    *A61B 5/024*     (2006.01)
    *A61B 5/022*     (2006.01)

(52) U.S. Cl.
    CPC ...... *A61B 5/02225* (2013.01); *A61B 5/02255* (2013.01); *F04B 45/047* (2013.01)

(58) Field of Classification Search
    USPC ............................................. 310/316.03, 317
    See application file for complete search history.

(56) References Cited

U.S. PATENT DOCUMENTS

2007/0185401 A1*   8/2007   Quinn ................... A61B 5/0225
                                                       600/485
2009/0045696 A1    2/2009   Suzuki
2009/0054794 A1*   2/2009   Shirasaki ........... A61B 5/02233
                                                       600/490
2009/0224818 A1*   9/2009   Yoneyama ............ H02M 7/538
                                                       327/333
2010/0331667 A1   12/2010   Nelson
2011/0068657 A1    3/2011   Sunaga et al.
2011/0190670 A1*   8/2011   Jaeb ..................... F04B 43/046
                                                          601/6

FOREIGN PATENT DOCUMENTS

| JP | 2004-048902 A | 2/2004 |
| JP | 2009-050051 A | 3/2009 |
| JP | 2010-142783 A | 7/2010 |
| JP | 2010-148325 A | 7/2010 |
| JP | 2011-87455 A | 4/2011 |

OTHER PUBLICATIONS

Official Communication issued in International Patent Application No. PCT/JP2013/060231, dated May 7, 2013.

* cited by examiner

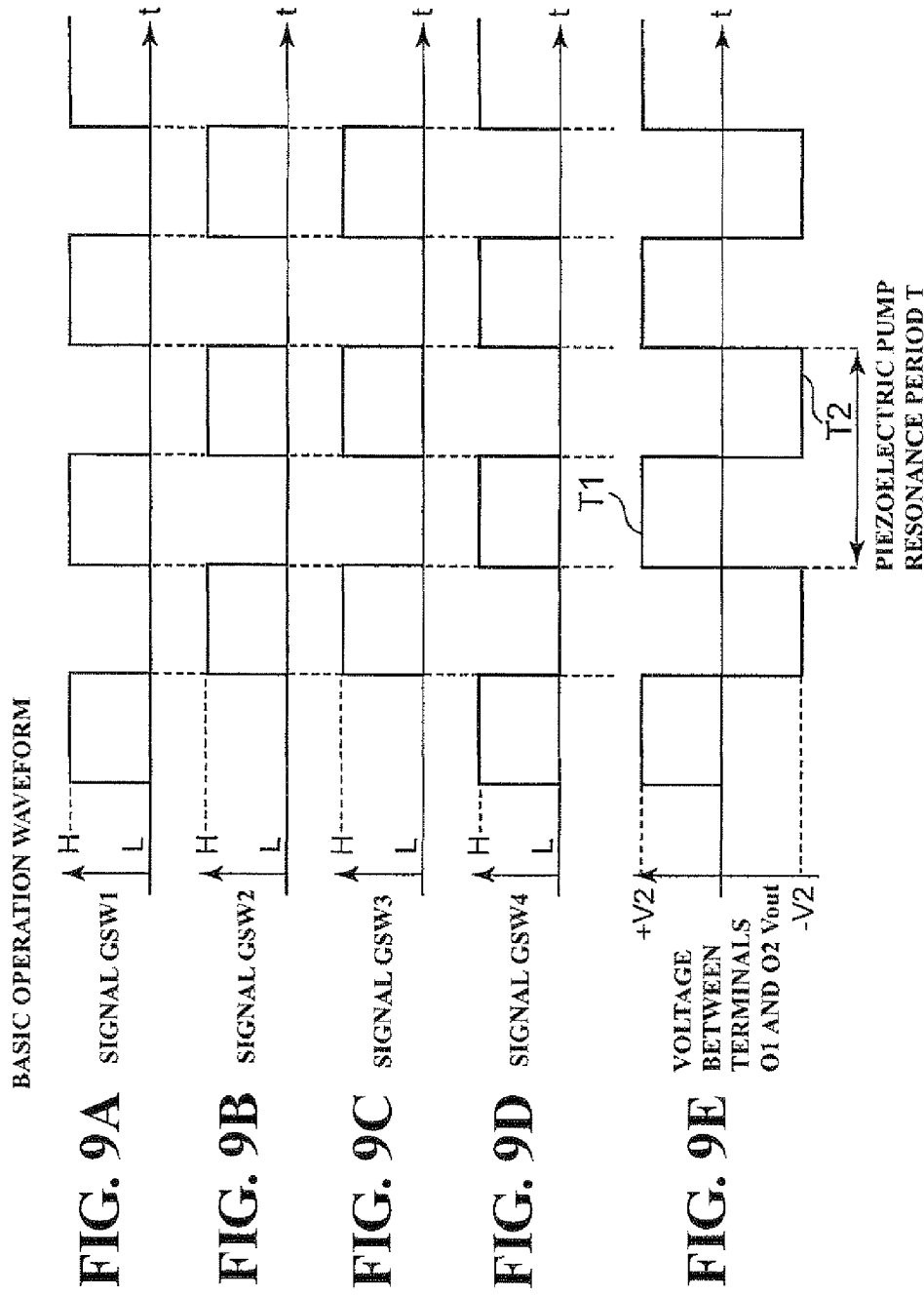

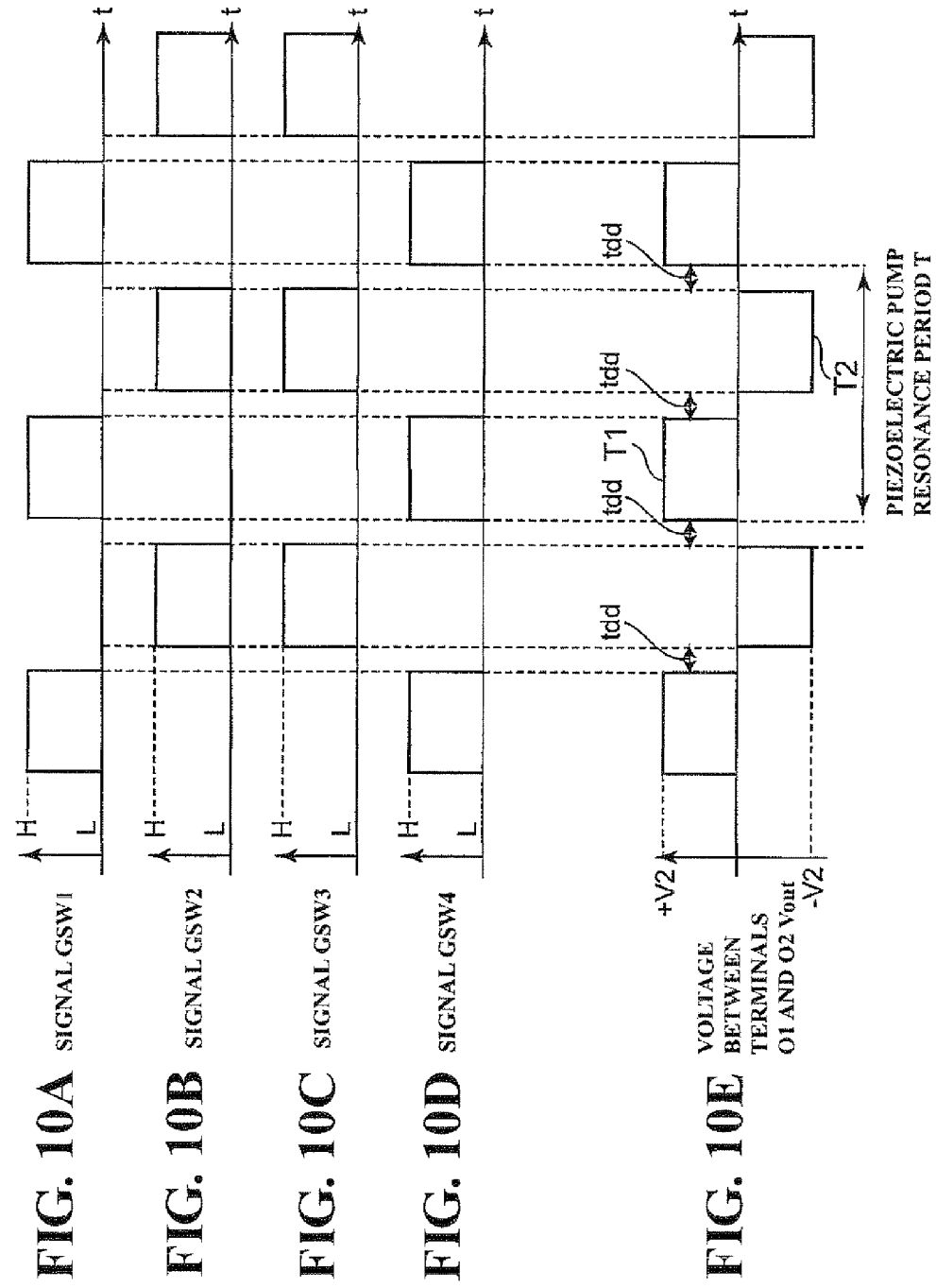

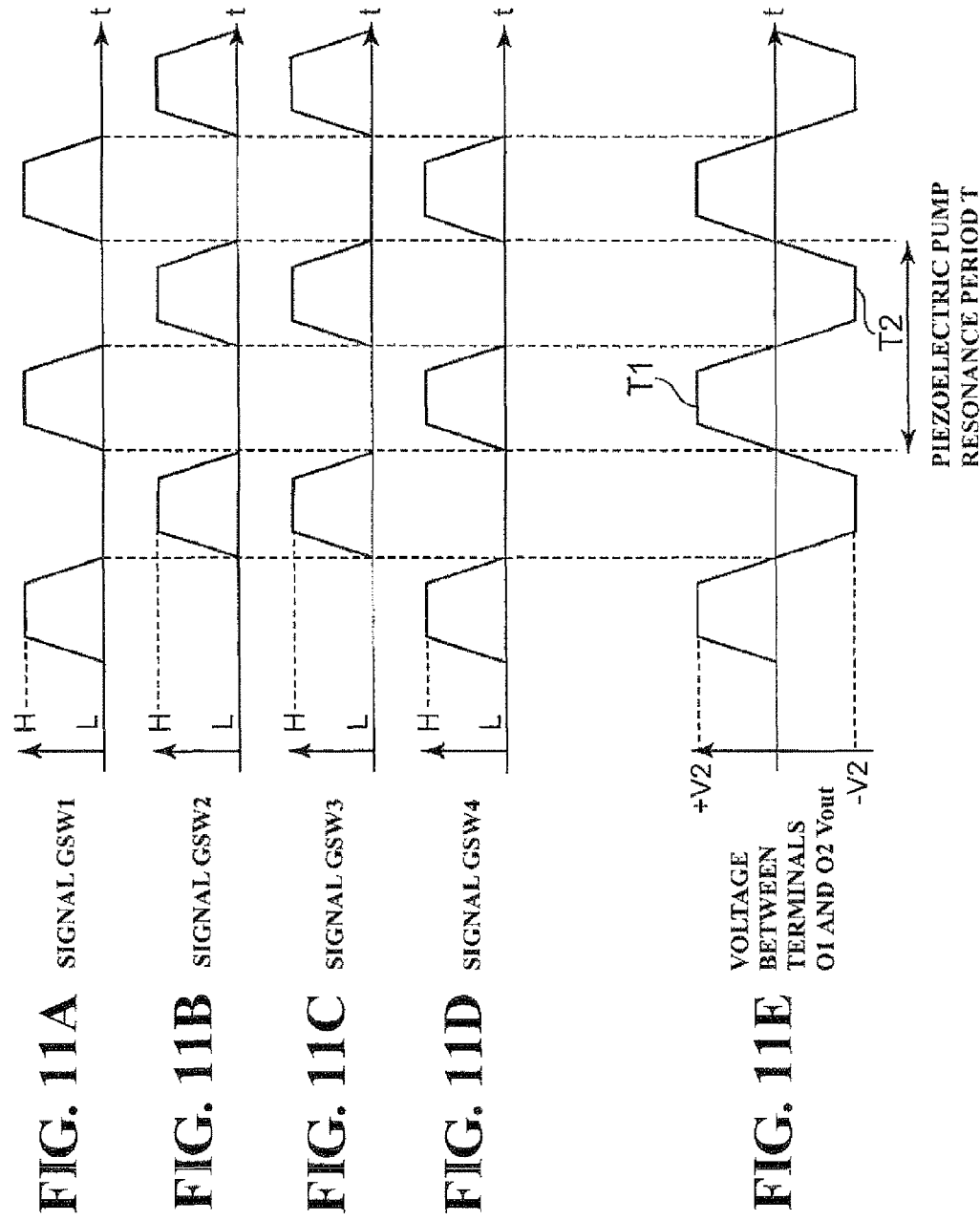

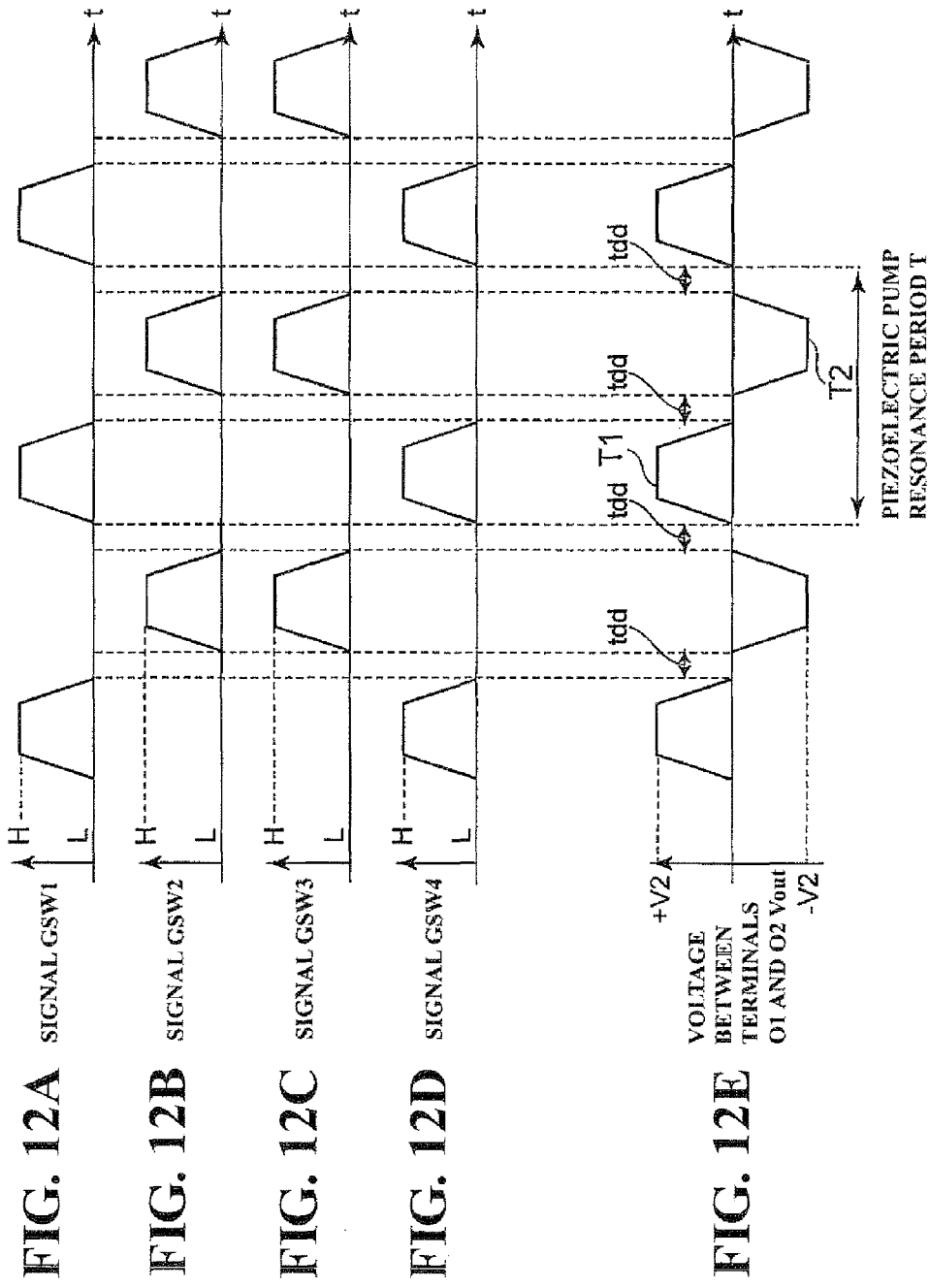

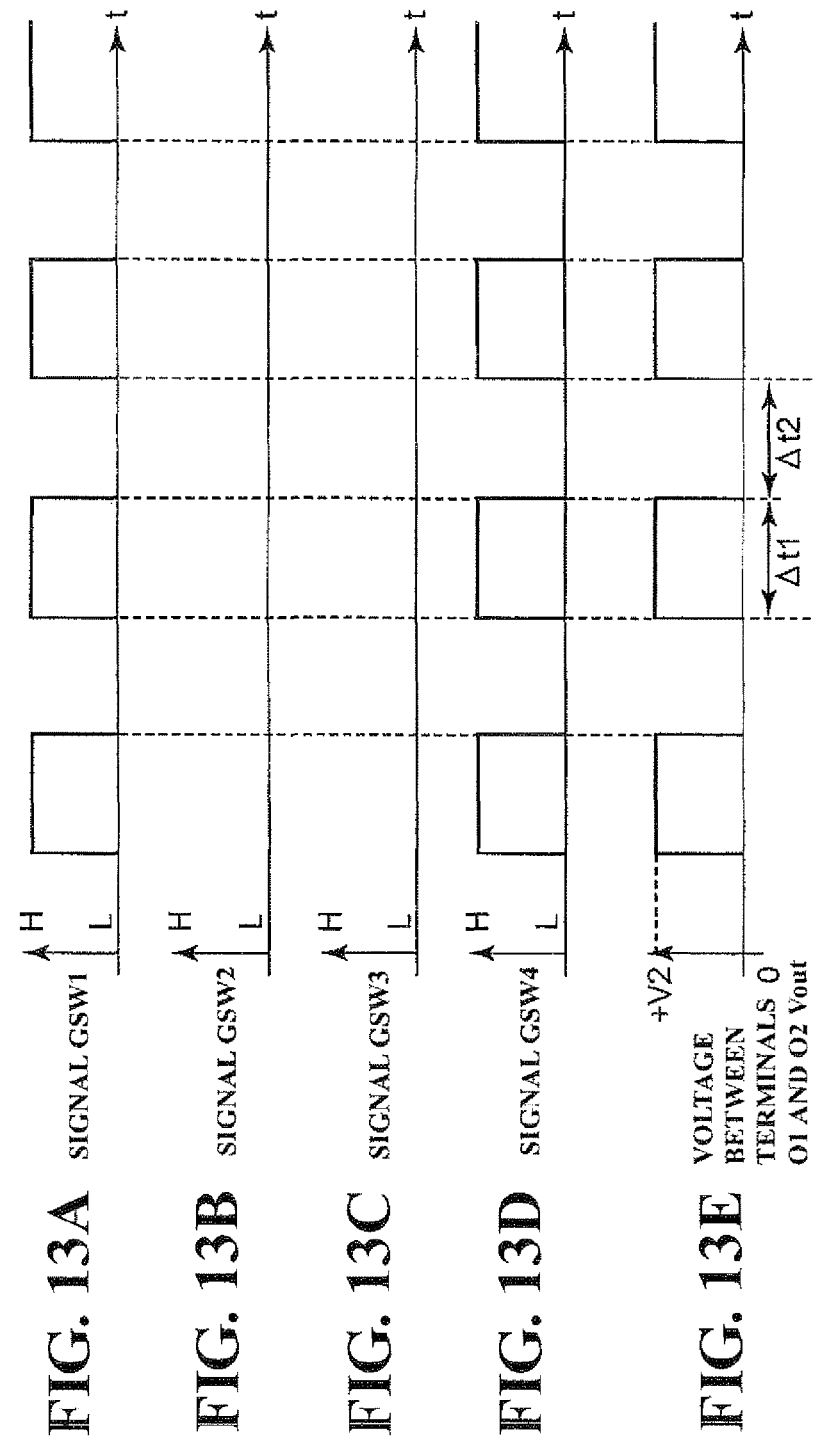

BLOOD PRESSURE METER AND PUMP DRIVING SYSTEM

TECHNICAL FIELD

The present invention relates to a blood pressure meter, and more specifically relates to a blood pressure meter including a pump that send a fluid to a blood pressure measurement cuff, and a pump driving circuit for driving the pump.

Also, the invention relates to a pump driving system that includes a pump and a pump driving circuit for driving the pump.

BACKGROUND ART

Recently, as disclosed in Patent Literature 1 (JP 2000-171320A) for example, it has been proposed that a piezoelectric pump (a pump that drives a diaphragm using a piezoelectric element) is used as a pump for sending fluid to a blood pressure measurement cuff (refers more accurately to an air bladder contained in a cuff. The same follows below.) of a blood pressure meter.

For example, as disclosed in Patent Literature 2 (JP 2010-142783A), as a publicly-known driving circuit for driving a piezoelectric pump, there is known to be a method of stepping up a low-voltage power supply so as to generate a high-voltage driving power supply for a piezoelectric element, amplifying the low-voltage driving waveform using an amplifier while using the driving power supply, and obtaining a driving signal for driving the piezoelectric element. Also, as disclosed in Patent Literature 3 (JP 2009-50051A), there is known to be a method in which the power supply voltage is switched (according to the driving frequency for the piezoelectric element) on the primary side of a transformer, and the driving voltage is applied to the piezoelectric element that is connected to the secondary side of the transformer.

CITATION LIST

Patent Literature

Patent Literature 1: JP 2000-171320A
Patent Literature 2: JP 2010-142783A
Patent Literature 3: JP 2009-50051A

SUMMARY OF INVENTION

Technical Problem

Here, in the case where a piezoelectric pump is used as a pump that sends a fluid to the blood pressure measurement cuff of a wrist blood pressure meter for example, it is desirable that the driving signal for driving the piezoelectric pump (the piezoelectric element thereof) has a maximum amplitude of 50 Vp-p (peak-to-peak voltage), for example. In addition, in order to perform inflation at a constant speed (e.g., 10 mmHg/sec) and adapt to variation in the characteristics of the piezoelectric pump, it is preferable that the amplitude is finely controlled in units of 0.1 V and the driving frequency is finely controlled in units of 100 Hz, for example.

However, with the method disclosed in Patent Literature 2 (JP 2010-142783A), a large-scale power supply that provides a predetermined high voltage is required as the power supply (high-voltage driving power supply) for the amplifier, and the amplifier also increases in cost. Also, it is difficult to finely control the amplitude and driving frequency. For this reason, there is a problem in that a smaller size, a lower cost, and improved performance cannot be achieved.

Similarly, with the method disclosed in Patent Literature 3 (JP 2009-50051A), the transformer has a larger size and a higher cost. Also, it is difficult to finely control the amplitude and driving frequency. For this reason, there is a problem in that a smaller size, a lower cost, and improved performance cannot be achieved.

In view of this, it is an object of the invention to provide a blood pressure meter including a pump that sends a fluid to a blood pressure measurement cuff and a pump driving circuit for driving the pump, by which it is possible to achieve a smaller size, a lower cost, and improved performance.

Also, it is an object of the invention to provide a pump driving system that includes a pump and a pump driving circuit for driving the pump, by which it is possible to achieve a smaller size, a lower cost, and improved performance.

Solution to Problem

In order to solve the above-described problem, a blood pressure meter according to the present invention includes at least:

a pump configured to send a fluid to a blood pressure measurement cuff;

a pump driving circuit for driving the pump; and a control unit configured to control the pump driving circuit in order to measure blood pressure, wherein the pump driving circuit includes:

a step-up unit that steps up a first DC voltage from a power supply and outputs it as a second DC voltage, and an H bridge unit that has first and second series circuits that each include two switching elements that are connected in series between a high potential corresponding to the second DC voltage and a reference potential that is lower than the high potential, the two switching elements of the first series circuit and the two switching elements of the second series circuit are switched on and off using bridge control signals from the control unit, and a voltage that is generated between a first contact point between the two switching elements of the first linear circuit and a second contact point between the two switching elements of the second linear circuit is used as a driving voltage for driving the pump.

With the blood pressure meter according to the invention, the step-up unit steps up a first DC voltage from a power supply and outputs it as a second DC voltage. The first and second linear circuits included in the H bridge unit are each connected between a high potential corresponding to the second DC voltage and a reference potential (e.g., a grounding potential) that is lower than the high potential. The two switching elements of the first series circuit and the two switching elements of the second series circuit are switched on and off using the bridge control signals from the control unit. A voltage that is generated between a first contact point between the two switching elements of the first series circuit and a second contact point between the two switching elements of the second series circuit is used as a driving voltage for driving the pump.

For example, the pump is a piezoelectric pump, and the two switching elements of the first series circuit are switched on and off in a complimentary manner using the bridge control signals from the control unit, and the two switching elements of the second series circuit are switched on and off in a complimentary manner with a phase that is the inverse of that of the switching on and off of the two switching elements of the first series circuit. In this case, in order to obtain a driving voltage that has an amplitude of around 50 Vp-p (peak to peak voltage) for example, it is sufficient that the step-up unit outputs a voltage that is half of the amplitude required for the driving voltage, or in other words, a maximum of 25 V, as the second DC voltage. Accordingly, the power supply can also be configured by a 3-V dry-cell battery (1.5 V×2), for example. Also, the step-up unit can be configured to have a smaller size and a lower cost. Furthermore, the H bridge unit itself can also be configured to have a smaller size and a lower cost due to the fact that it has relatively few parts.

Also, in order to switch the two switching elements of the first series circuit and the two switching elements of the second series circuit on and off, the control unit need only output four digital signals as the bridge control signals, and therefore the load is small. Accordingly, the control unit can be constituted by an existing CPU (Central Processing Unit) that is included in a blood pressure meter for example, without providing a special new part. Also, if digital signals, for example, PWM (Pulse Width Modulation) signals output by this kind of CPU are used as the bridge control signals, it is possible to finely control switching on and off, and it is possible to finely control the driving frequency for the pump in units of 100 Hz, for example. Accordingly, variation in the properties of the piezoelectric pump (in particular, variation in the resonance frequency), for example, can be easily adapted to.

Accordingly, with the blood pressure meter, it is possible to achieve a smaller size, a lower cost, and improved performance.

Note that it is desirable that the blood pressure meter includes a pressure sensor that detects fluid pressure in the blood pressure measurement cuff, and a control unit that obtains the blood pressure measurement value of the measurement subject based on the output of the pressure sensor. According to this, the blood pressure measurement value of the measurement subject can be output.

With the blood pressure meter according to an embodiment, the step-up unit is a step-up regulator that varies and outputs the second DC voltage according to the step-up control signal from the control unit.

With the blood pressure meter according to an embodiment, the step-up unit is a step-up regulator that varies and outputs the second DC voltage according to the step-up control signal from the control unit. A small-sized and inexpensive step-up regulator that is commercially available can be employed as this kind of step-up regulator. Accordingly, with the blood pressure meter, it is possible to achieve an even smaller size and an even lower cost.

With the blood pressure meter according to an embodiment, the step-up control signal from the control unit is a PWM signal, and the step-up regulator serving as the step-up unit varies and outputs the second DC voltage according to the pulse width of the PWM signal.

With the blood pressure meter according to an embodiment, the step-up control signal from the control unit is a PWM (Pulse Width Modulation) signal, and therefore it is possible to finely control the switching on and off. The step-up regulator serving as the step-up unit varies and outputs the second DC voltage according to the pulse width of the PWM signal. For example, it is possible to finely step up the second DC voltage in units of 0.1 V. Accordingly, if the pump is a piezoelectric pump, for example, inflation at a constant speed (e.g., 10 mmHg/sec) can be performed easily. Accordingly, with the blood pressure meter, it is possible to achieve a further improved performance.

With the blood pressure meter according to an embodiment, the pump is a piezoelectric pump, and according to the bridge control signals from the control unit, the two switching elements of the first series circuit are switched on and off in a complimentary manner, and the two switching elements of the second series circuit are switched on and off in a complimentary manner with a phase that is the inverse of that of the switching on and off of the two switching elements of the first series circuit.

Here, a "piezoelectric pump" is a pump that includes a piezoelectric element and a diaphragm coupled with the piezoelectric element, and the diaphragm oscillates together with the piezoelectric element due to an AC voltage being applied to the piezoelectric element, and thereby a fluid is sent using the oscillation of the diaphragm.

With the blood pressure meter according to an embodiment, the two switching elements of the first series circuit are switched on and off in a complimentary manner, and the two switching elements of the second series circuit are switched on and off in a complimentary manner with a phase that is the inverse of that of the switching on and off of the two switching elements of the first series circuit according to the bridge control signals from the control unit. Accordingly, an AC voltage is applied as a driving voltage to the piezoelectric pump serving as the pump. Accordingly, it is possible for the piezoelectric pump to operate so as to send a fluid to the blood pressure measurement cuff. Here, in order to obtain a driving voltage that has an amplitude of around 50 Vp-p (peak-to-peak voltage), for example, it is sufficient that the step-up unit outputs a voltage that is half of the amplitude required for the driving voltage, or in other words, a maximum of 25 V, as the second DC voltage. Accordingly, the power supply can be configured by a 3-V dry-cell battery (1.5 V×2), for example. Also, the step-up unit can be configured to have a smaller size and a lower cost. Furthermore, the H bridge unit itself can also be configured to have a smaller size and a lower cost due to the fact that it has relatively few parts.

Also, in order to switch the two switching elements of each of the first and second series circuit on and off, the control unit need only output four digital signals as the bridge control signals, and therefore the load is small. Accordingly, the control unit can be constituted by an existing CPU that is included in a blood pressure meter for example, without providing a special new part. Also, according to the digital signals output by this kind of CPU as the bridge control signals, for example, PWM signals, the switching on and off can be finely controlled and the driving frequency for the pump can be finely controlled. Accordingly, variation in the properties of the piezoelectric pump, for example, can be easily adjusted.

Accordingly, with the blood pressure meter, it is possible to achieve an even smaller size, an even lower cost, and an even higher performance.

With the blood pressure meter according to an embodiment, the control unit performs control for setting a rest period in which all switching elements are off between an on period of a switching element in each of the first and second series circuits and an on period of another switching element that follows the on period.

With the blood pressure meter according to an embodiment, the control unit performs control for setting a rest period in which all switching elements are off between an on period of a switching element in each of the first and second series circuits and an on period of other switching element that follows the on period. Accordingly, in the waveform of the driving voltage for the piezoelectric pump serving as the pump, a period of zero applied voltage appears between a period of applying a positive voltage and a period of applying a negative voltage. As a result, when the driving voltage is reversed, or in other words, when the period of applying the positive voltage is started or the period of applying the negative voltage is started, inrush currents with respect to the piezoelectric pump serving as the pump are restricted. Accordingly, power consumption at the time of reversing the driving voltage is suppressed, and energy conservation is realized.

With the blood pressure meter according to an embodiment, the control unit performs control for causing the switching elements of the first and second series circuits to transition from an off state to an on state and from the on state to the off state over finite transition periods.

With the blood pressure meter according to an embodiment, the control unit performs control for causing the switching elements of the first and second series circuits to transition from an off state to an on state and from the on state to the off state over finite transition periods. Accordingly, in the waveform of the driving voltage for the piezoelectric pump serving as the pump, when a period of applying a positive voltage is started or ended or a period of applying a negative voltage is started or ended, the applied voltage is transitioned over a finite transition period. As a result, when the driving voltage is reversed, or in other words, when the period of applying the positive voltage is started or the period of applying the negative voltage is started, inrush currents with respect to the piezoelectric pump serving as the pump are restricted. Accordingly, power consumption at the time of reversing the driving voltage is suppressed, and energy conservation is realized.

With the blood pressure meter according to an embodiment, the pump is a rotary pump, and according to the bridge control signals from the control unit, among the two switching elements of the first series circuit, the switching element on the high-potential side is switched on and off, and the switching element on the reference potential side is kept in the off state, and among the two switching elements of the second series circuit, the switching element on the high-potential side is kept in the off state, and the switching element on the reference potential side is switched on and off with a phase that is the inverse of that of the switching on and off of the switching element on the high-potential side of the first series circuit.

With the blood pressure meter according to an embodiment, the pump is a rotary pump. According to the bridge control signals from the control unit, among the two switching elements of the first series circuit, the switching element on the high-potential side is switched on and off, and the switching element on the reference potential side is kept in the off state, and among the two switching elements of the second series circuit, the switching element on the high-potential side is kept in the off state, and the switching element on the reference potential side is switched on and off with a phase that is the inverse of that of the switching on and off of the switching element on the high-potential side of the first series circuit. Accordingly, a periodic positive voltage is applied as a driving voltage to the rotary pump serving as the pump. Accordingly, the rotary pump can operate so as to send a fluid to the blood pressure measurement cuff.

A pump driving system according to the present invention includes at least:

a pump;

a pump driving circuit for driving the pump; and a control unit configured to control the pump driving circuit, wherein the pump driving circuit includes:

a step-up unit that steps up a first DC voltage from a power supply and outputs it as a second DC voltage, and an H bridge unit that has first and second series circuits that each include two switching elements that are connected in series between a high potential corresponding to the second DC voltage and a reference potential that is lower than the high potential, the step-up control signal from the control unit is a PWM signal, and the step-up unit is a step-up regulator that includes a first resistance unit that includes a resistor and a FET and can vary the resistance value according to the pulse width of the PWM signal, and a second resistance unit, and can vary and output the second DC voltage by dividing the second DC voltage between the first resistance unit and the second resistance unit and causing it to be fed back, the two switching elements of each of the first and second series circuits are switched on and off using the bridge control signals from the control unit, and a voltage that is generated between a first contact point between the two switching elements of the first series circuit and a second contact point between the two switching elements of the second series circuit is used as a driving voltage for driving the pump.

In the pump driving system according to the present invention, the step-up unit steps up a first DC voltage from a power supply and outputs it as a second DC voltage. The first and second series circuits included in the H bridge unit are each connected between a high potential corresponding to the second DC voltage and a reference potential (e.g., a grounding potential) that is lower than the high potential. The two switching elements of the first series circuit and the two switching elements of the second series circuit are switched on and off using the bridge control signals from the control unit. A voltage that is generated between a first contact point between the two switching elements of the first series circuit and a second contact point between the two switching elements of the second series circuit is used as a driving voltage for driving the pump.

For example, the pump is a piezoelectric pump, and the two switching elements of the first series circuit are switched on and off in a complimentary manner using the bridge control signals from the control unit, and the two switching elements of the second series circuit are switched on and off in a complimentary manner with a phase that is the inverse of that of the switching on and off of the two switching elements of the first series circuit. In this case, in order to obtain a driving voltage that has an amplitude of around 50 Vp-p (peak-to-peak voltage) for example, it is sufficient that the step-up unit outputs a voltage that is half of the amplitude required for the driving voltage, or in other words, 25 V at most, as the second DC voltage. Accordingly, the power supply can be configured by a 3-V dry-cell battery (1.5 V×2), for example. Also, the step-up unit can be configured to have a smaller size and a lower cost. Furthermore, the H bridge unit itself can also be configured to have a smaller size and a lower cost due to the fact that it has relatively few parts.

Also, in order to switch the two switching elements of the first series circuit and the two switching elements of the second series circuit on and off, the control unit need only output four digital signals as the bridge control signals, and therefore the load is small. Accordingly, the control unit can be constituted by a CPU (Central Processing Unit). Also, if digital signals, for example, PWM (Pulse Width Modulation) signals output by this kind of CPU are used as the bridge control signals, it is possible to finely control switching on and off, and it is possible to finely control the driving frequency for the pump in units of 100 Hz, for example. Accordingly, variation in the properties of the piezoelectric pump (in particular, variation in the resonance frequency), for example, can be easily adapted to.

Furthermore, the step-up unit is a step-up regulator that includes a first resistance unit that includes a resistor and a FET and varies the resistance value according to the pulse width of the PWM signal, and a second resistance unit, divides the second DC voltage between the first resistance unit and the second resistance unit and causes it to be fed back. According to this, it is possible to vary and output the second DC voltage according to a voltage division ratio, or in other words, according to (resistance value of first resistance unit)/(resistance value of first resistance unit+resistance value of second resistance unit).

Accordingly, with the pump driving system, it is possible to achieve a smaller size, a lower cost, and improved performance.

With the pump driving system according to an embodiment, the pump is a piezoelectric pump, and according to the bridge control signals from the control unit, the two switching elements of the first series circuit are switched on and off in a complimentary manner, and the two switching elements of the second series circuit are switched on and off in a complimentary manner with a phase that is the inverse of that of the switching on and off of the two switching elements of the first series circuit.

With the pump driving system according to an embodiment, according to the bridge control signals from the control unit, the two switching elements of the first series circuit are switched on and off in a complimentary manner, and the two switching elements of the second series circuit are switched on and off in a complimentary manner with a phase that is the inverse of that of the switching on and off of the two switching elements of the first series circuit. Accordingly, an AC voltage is applied as a driving voltage to the piezoelectric pump serving as the pump. Accordingly, it is possible for the piezoelectric pump to operate so as to send a fluid to the blood pressure measurement cuff. Here, in order to obtain a driving voltage that has an amplitude of around 50 Vp-p (peak-to-peak voltage), for example, it is sufficient that the step-up unit outputs a voltage that is half of the amplitude required for the driving voltage, or in other words, a maximum of 25 V, as the second DC voltage. Accordingly, the power supply can be configured by a 3-V dry-cell battery (1.5 V×2), for example. Also, the step-up unit can be configured to have a smaller size and a lower cost. Furthermore, the H bridge unit itself can also be configured to have a smaller size and a lower cost due to the fact that it has relatively few parts.

With the pump driving system according to an embodiment, the control unit performs control for setting a rest period in which all switching elements are off between an on period of a switching element in each of the first and second series circuits and an on period of another switching element that follows the on period.

With the pump driving system according to an embodiment, the control unit performs control for setting a rest period in which all switching elements are off between an on period of a switching element in each of the first and second series circuits and an on period of another switching element that follows the on period. Accordingly, in the waveform of the driving voltage for the piezoelectric pump serving as the pump, a period of zero applied voltage appears between a period of applying a positive voltage and a period of applying a negative voltage. As a result, when the driving voltage is reversed, or in other words, when the period of applying the positive voltage is started or the period of applying the negative voltage is started, inrush currents with respect to the piezoelectric pump serving as the pump are restricted. Accordingly, power consumption at the time of reversing the driving voltage is suppressed, and energy conservation is realized.

With the pump driving system according to an embodiment, the control unit performs control for causing the switching elements of the first and second series circuits to transition from an off state to an on state and from the on state to the off state over finite transition periods.

With the pump driving system according to an embodiment, the control unit performs control for causing the switching elements of the first and second series circuits to transition from an off state to an on state and from the on state to the off state over finite transition periods. Accordingly, in the waveform of the driving voltage for the piezoelectric pump serving as the pump, when a period of applying a positive voltage is started or ended or a period of applying a negative voltage is started or ended, the applied voltage transitions over a finite transition period. As a result, when the driving voltage is reversed, or in other words, when the period of applying the positive voltage is started or the period of applying the negative voltage is started, inrush currents with respect to the piezoelectric pump serving as the pump are restricted. Accordingly, power consumption at the time of reversing the driving voltage is suppressed, and energy conservation is realized.

Advantageous Effects of the Invention

As can be understood from the description above, with the blood pressure meter and pump driving system of the invention, it is possible to achieve a smaller size, a lower cost, and improved performance.

BRIEF DESCRIPTION OF DRAWINGS

FIGS. 9 and 9A-9E are diagrams showing an example of waveforms of a control signal for the switching elements of the H bridge circuit and the driving voltage for the piezoelectric pump serving as the pump.

FIGS. 10 and 10A-10E are diagrams showing another example of waveforms of a control signal for the switching elements of the H bridge circuit and the driving voltage for the piezoelectric pump serving as the pump.

FIGS. 11 and 11A-11E are diagrams showing yet another example of waveforms of a control signal for the switching elements of the H bridge circuit and the driving voltage for the piezoelectric pump serving as the pump.

FIGS. 12 and 12A-12E are diagrams showing yet another example of waveforms of a control signal for the switching elements of the H bridge circuit and the driving voltage for the piezoelectric pump serving as the pump.

FIGS. 13 and 13A-13E are diagrams showing an example of waveforms of control signals for the switching elements of the H bridge circuit and the driving voltages for a rotary pump serving as the pump.

DESCRIPTION OF EMBODIMENTS

The invention will be described below in detail according to the illustrated embodiment.

Figure 1:
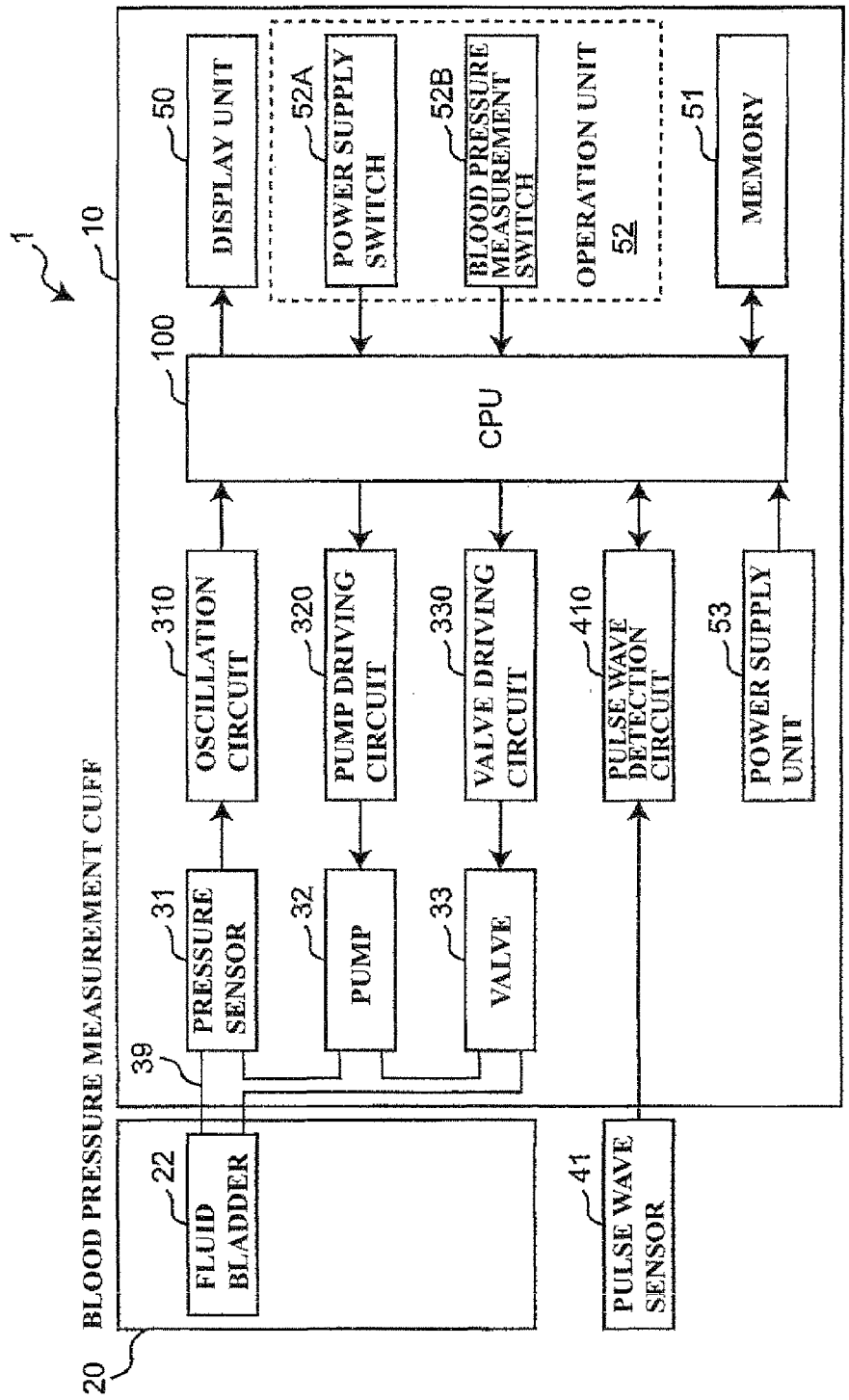
FIG. 1 is a diagram showing a schematic block configuration of a blood pressure meter according to an embodiment of the invention.

FIG. 1 shows a schematic block configuration of a blood pressure meter (indicated overall by reference numeral 1) according to an embodiment of the invention. The blood pressure meter 1 includes a main body 10, CPU (Central Processing Unit) 100 serving as a control unit mounted in the main body 10, a display unit 50, a memory 51, an operation unit 52, a power supply unit 53, a pump 32, a valve 33, and a pressure sensor 31. Also, the main body 10 has an oscillation circuit 310 that converts an output from the pressure sensor 31 into a frequency, a pump driving circuit 320 that drives the pump 32, a valve driving circuit 330 that drives the valve 33, and a pulse wave detection circuit 410 that controls the pulse wave sensor 41 so as to detect pulse waves. These elements are mounted in the main body 10.

The display unit 50 includes a display, an indicator, and the like, and displays predetermined information in accordance with a control signal from the CPU 100.

The operation unit 52 includes a power supply switch 52A that receives input of an instruction for switching the power supply unit 53 on or off, and a blood pressure measurement switch 52B for receiving an instruction to start blood pressure measurement. The power supply switch 52A and the blood pressure measurement switch 52B input an operation signal corresponding to an instruction given by an operator to the CPU 100.

The memory 51 stores data for programs for controlling the blood pressure meter 1, data used for controlling the blood pressure meter 1, setting data for setting various functions of the blood pressure meter 1, data regarding measurement results of a blood pressure value and a pulse rate, and the like. Also, the memory 51 is used as a working memory or the like for when a program is executed.

The CPU 100 performs control for driving the pump 32, the valve 33, and the pulse wave sensor 41 according to an operation signal from the operation unit 52, in accordance with a program stored in the memory 51 for controlling the blood pressure meter 1. Also, the CPU 100 calculates the blood pressure value and pulse rate based on a signal from the pressure sensor 31 and the pulse wave sensor 41 and controls the display unit 50 and the memory 51.

The power supply unit 53 supplies power to the CPU 100, the pressure sensor 31, the pump 32, the valve 33, the pulse wave sensor 41, the display unit 50, the memory 51, the oscillation circuit 310, the pump driving circuit 320, the valve driving circuit 330, and the pulse wave detection circuit 410. In this example, the power supply unit 53 is configured by connecting two dry-cell batteries (1.5 V) in a series and supplies 3 V as a first DC voltage.

In this example, the pump 32 is composed of a piezoelectric pump and supplies air to the fluid bladder 22 in order to increase the internal pressure of the fluid bladder 22 (cuff pressure). The valve 33 controls the cuff pressure by opening and closing so as to discharge air from the fluid bladder 22 or seal it. The pump driving circuit 320 drives the pump 32 based on a control signal provided by the CPU 100. The valve driving circuit 330 opens and closes the valve 33 based on the control signal provided by the CPU 100.

The pressure sensor 31 is, for example, a piezoresistant pressure sensor and is connected to the pump 32, the valve 33, and fluid bladder 22 that is contained in the cuff 20, via a cuff air tube 39. In this example, the oscillation circuit 310 oscillates based on an electric signal value that is based on a change in electric resistance caused by a piezoresistant effect from the pressure sensor 31 and outputs a frequency signal having a frequency corresponding to the electric signal value of the pressure sensor 31 to the CPU 100.

The pulse wave detection circuit 410 is connected to the pulse wave sensor 41 and the CPU 100. The pulse wave detection circuit 410 has a light emitting element driving circuit (not shown) that drives a light emitting element 411 of the pulse wave sensor 41 based on a control signal from the CPU 100, and a received light amount detection circuit (not shown) that generates a voltage signal based on the output signal from a light receiving element 412.

The light emitting element driving circuit causes the light emitting element 411 to emit light by applying a predetermined amount of current to the light emitting element 411 based on a control signal from the CPU 100. A DC current of around 50 mA, for example, is used as the current that is applied to the light emitting element 411. Preferably, as the light emitting element driving circuit, a circuit is used that periodically causes the light emitting element 411 to emit pulses of light by supplying the pulse current with a predetermined duty to the light emitting element 411. Thus, by causing the light emitting element 411 to emit pulses of light, it is possible to suppress the amount of power applied to the light emitting element 411 per unit time, and it is possible to prevent a rise in temperature of the light emitting element 411.

The received light amount detection circuit includes processing circuits such as an analog filter circuit, a rectifying circuit, an amplifying circuit, and an A/D (Analog/Digital) conversion circuit, and the output signal received from the light receiving element 412 as an analog value is output as a digitized voltage signal to the CPU 100 by the received light amount detection circuit.

Figure 2:
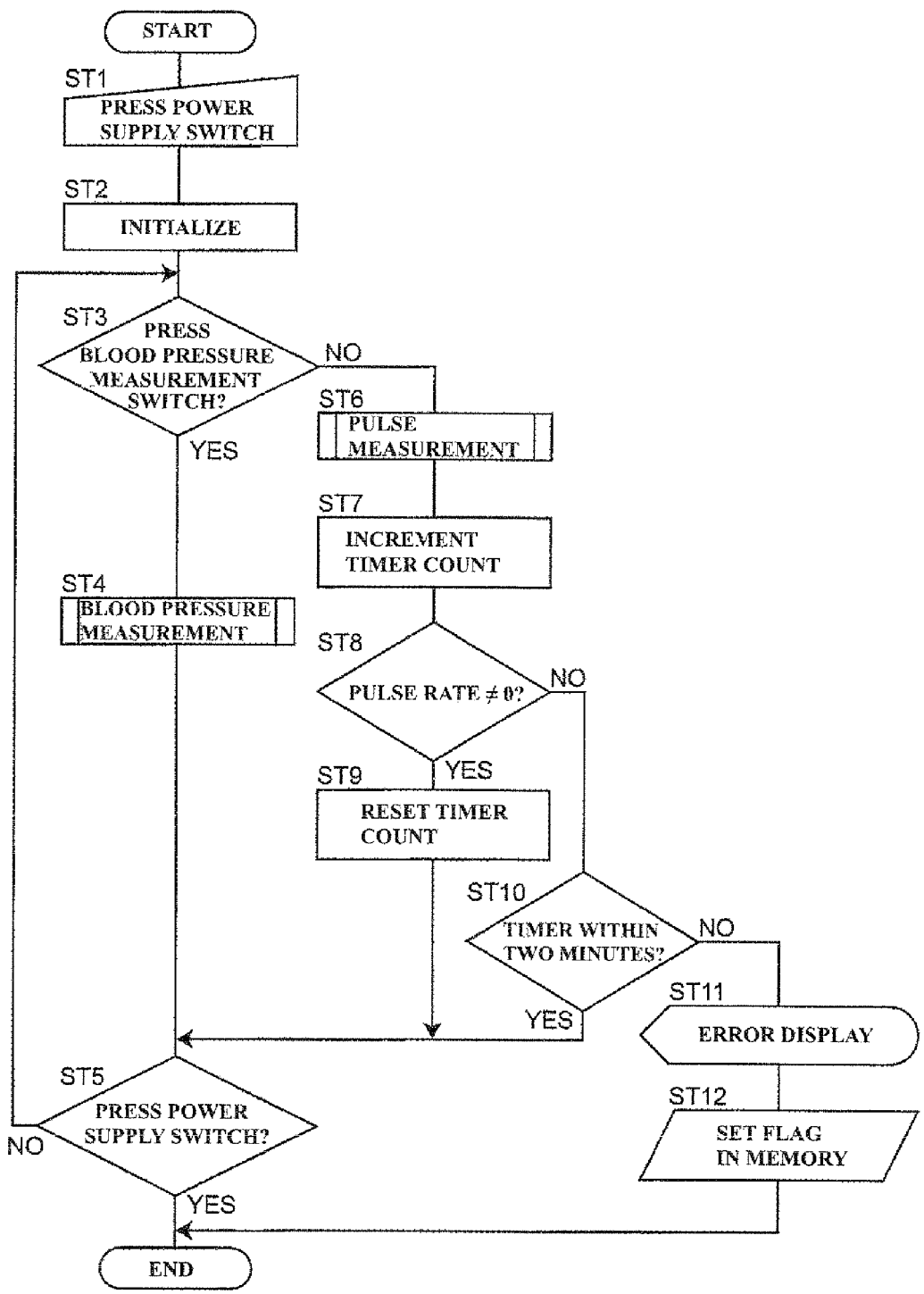
FIG. 2 is a flowchart for describing operations of a control unit of the blood pressure meter.

The measurement of the blood pressure and pulse rate is performed by the CPU 100 of the blood pressure meter 1 according to the flow in FIG. 2.

Before the blood pressure measurement method of the present embodiment is described, the principle of blood pressure measurement performed using a general oscillometric method will be described.

In the case of measuring blood pressure using a general oscillometric method, the following operations are performed. That is to say, the cuff is wrapped around the measurement site of the measurement subject in advance, and at the time of measurement, the pump and valve are controlled so as to increase the cuff pressure such that it is greater than the maximum blood pressure and gradually reduce the cuff pressure thereafter. In the process of reducing the cuff pressure, variation in the arterial volume that is generated in the artery of the measurement site is detected as a pulse wave signal by the pressure sensor via the cuff. The cuff pressure at that time and the size of the detected variation in the arterial volume (the amplitude of the pulse wave signal) are used to calculate the maximum blood pressure (Systolic Blood Pressure) and the minimum blood pressure (Diastolic Blood Pressure), and thereby the blood pressure is measured.

Specifically, in this example, the operator first switches on the power supply switch 52A of the blood pressure meter 1, thereby bringing it into the operating state (step ST1). Thereafter, the CPU 100 initializes the memory region for processing and outputs a control signal to the valve driving circuit 330. The valve driving circuit 330 discharges the air inside the fluid bladder 22 of the cuff 20 by releasing the valve 33 based on the control signal. Next, control for calibrating the pressure sensor 31 to 0 mmHg is performed (step ST2).

Next, the measurement subject attaches the cuff 20 by wrapping it around a wrist of the measurement subject. If the measurement subject presses the blood pressure measurement switch 52B after the cuff 20 has been wrapped around the wrist (YES in step ST3), the CPU 100 performs control for starting blood pressure measurement in accordance with the oscillometric method (step ST4).

Figure 3:
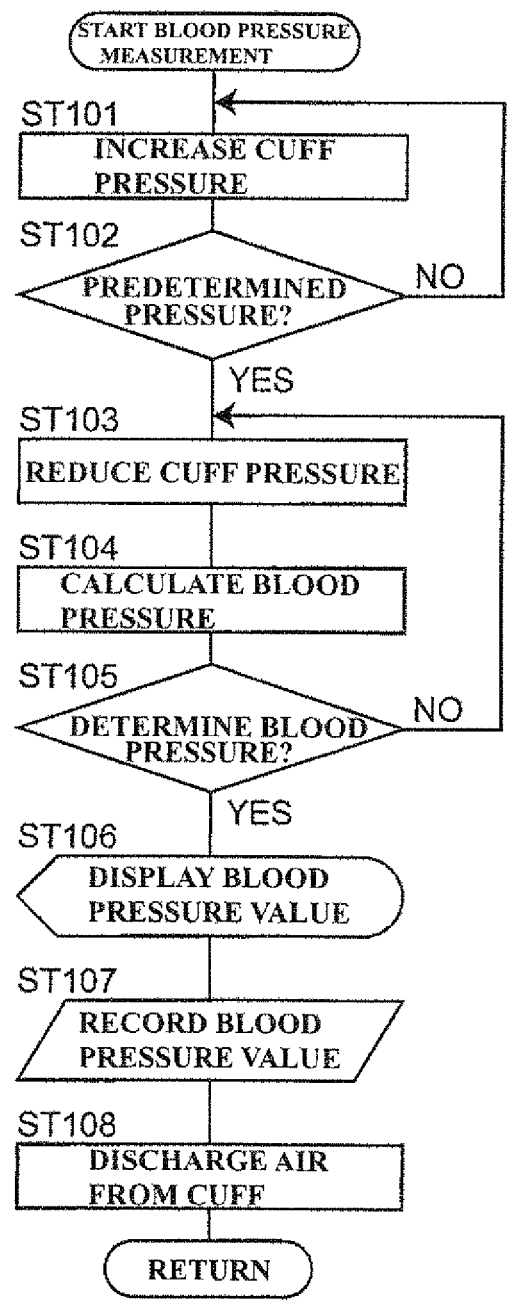
FIG. 3 is a flowchart for describing a blood pressure measurement operation performed by the control unit of the blood pressure meter.

As shown in FIG. 3, during blood pressure measurement, the CPU 100 first locks the valve 33 via the valve driving circuit 330 and thereafter performs control for driving the pump 32 via the pump driving circuit 320 so as to send air to the fluid bladder 22. This causes the fluid bladder 22 to expand and gradually increases the cuff pressure (step ST101).

When the cuff pressure is increased and reaches a predetermined pressure (YES in step ST102), the CPU 100 stops the pump 32 via the pump driving circuit 320 and thereafter performs control for gradually releasing the valve 33 via the valve driving circuit 330. This causes the fluid bladder 22 to contract and gradually reduces the cuff pressure (step ST103).

Here, the predetermined pressure is a pressure that is sufficiently higher than the systolic blood pressure (e.g., systolic blood pressure+30 mmHg), and it is stored in advance in the memory 51 or is determined by the CPU 100 estimating the systolic blood pressure using a predetermined equation while the cuff pressure is being increased.

In the process of deflation, volume change that occurs in an artery in the wrist is detected as a pressure pulse wave signal by the pressure sensor 31 via the cuff 20. Based on the pressure pulse wave signal, the CPU 100 calculates the blood pressure value by applying a predetermined algorithm according to the oscillometric method (step ST104). Note that the blood pressure may be calculated during the inflation step rather than the deflation step.

When the blood pressure value is determined by calculation (YES in step ST105), the CPU 100 display the calculated blood pressure value on the display unit 50 (step ST106) and performs control for storing the blood pressure value in the memory 51 (step ST107).

Next, the CPU 100 releases the valve 33 via the valve driving circuit 330 and performs control for discharging the air in the fluid bladder 22 of the cuff 20 (step ST108).

Next, as shown in FIG. 2, if the power supply switch 52A is not pressed (NO in step ST5), the CPU 100 returns to step ST3, and if the power supply switch 52A is pressed, measurement ends.

On the other hand, if the measurement subject has not pressed the blood pressure measurement switch 52B (NO in step ST3), the CPU 100 performs control for starting pulse measurement (step ST6).

Figure 4:
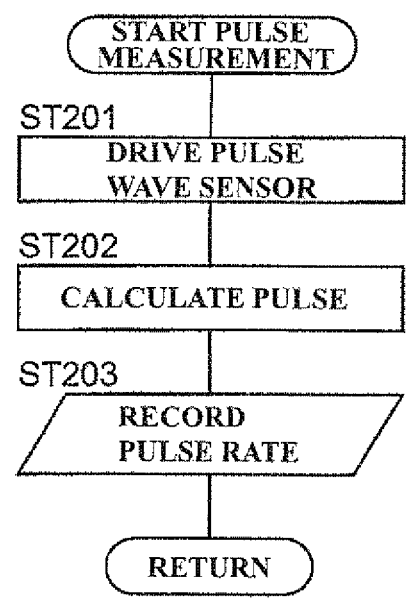
FIG. 4 is a flowchart for describing a pulse measurement operation performed by the control unit of the blood pressure meter.

As shown in FIG. 4, during pulse measurement, the CPU 100 first performs control for causing the light emitting element 411 to be driven via the light emitting element driving circuit of the pulse wave detection circuit 410 and causing the light emitting element 411 to emit light (step ST201). Note that by using a frequency (e.g., 3kHz) that is sufficiently higher than the frequency component included in the variation in the arterial volume that is to be detected (around 30 Hz) as the driving frequency of the light emitting element 411, the variation in the arterial volume can be detected with greater precision.

The light emitted from the light emitting element 411 to the artery that extends within the wrist is reflected by the artery, the reflected light is received by the light receiving element 412, and an output signal corresponding to the amount of received light is output. The received light amount detection circuit generates a voltage signal based on the output signal from the light receiving element 412 and outputs it to the CPU 100. Based on the voltage signal, the CPU 100 applies a predetermined algorithm so as to calculate the pulse rate (step ST202) and performs control for storing the calculated pulse rate in the memory 51 (step ST203).

Next, as shown in FIG. 2, the CPU 100 performs control for incrementing the timer count for measuring the pulse rate calculation operation time (step ST7). If a pulse wave is detected and it is determined that there is a pulse (YES in step ST8), the CPU 100 performs control for resetting the timer count (step ST9).

Next, if the power supply switch 52A is not pressed (NO in step ST5), the CPU 100 returns to step ST3, and if the power supply switch 52A is pressed, measurement ends.

On the other hand, if a pulse wave is not detected, the CPU 100 determines that there is no pulse (NO in step ST8) and if a pulse wave is furthermore not detected for 2 or more minutes (NO in step ST10), the CPU 100 performs control for causing an abnormality to be displayed on the display unit 50 (step ST11). Next, the CPU 100 performs control for setting a flag indicating that there is an abnormality in the memory 51 (step ST12) and ends measurement.

Figure 5:
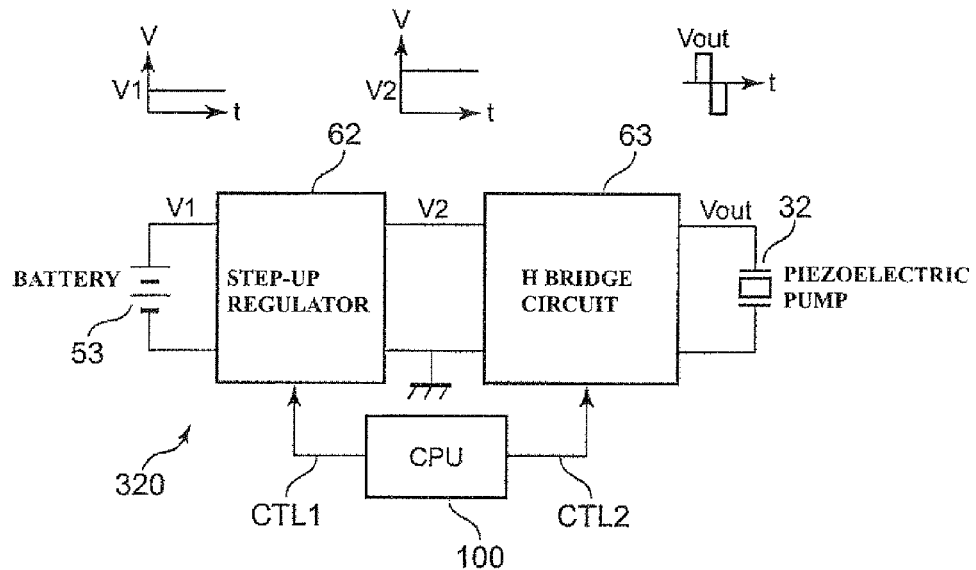
FIG. 5 is a diagram showing a block configuration of a pump driving circuit that drives a pump of the blood pressure meter.

FIG. 5 shows a block configuration of the pump driving circuit 320. The pump driving circuit 320 has a step-up regulator 62 serving as a step-up unit, and an H bridge circuit 63 serving as an H bridge unit.

Figure 6A:
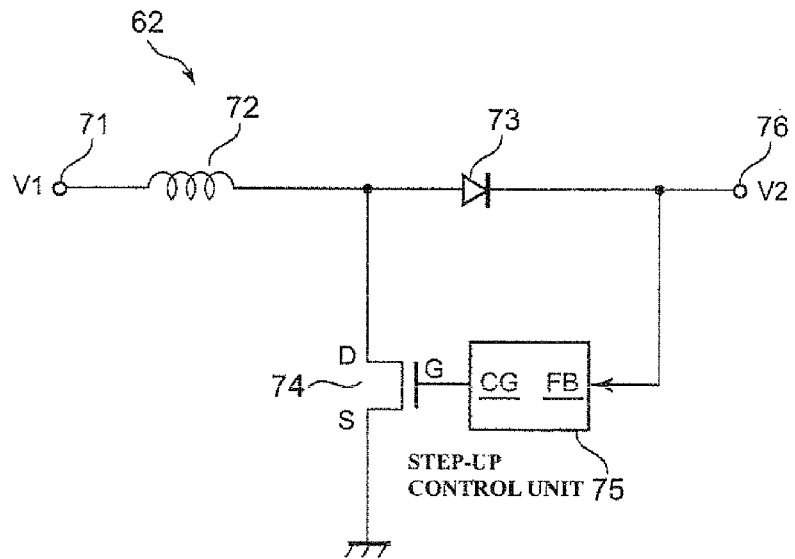
FIG. 6A is a diagram showing a block configuration of a step-up regulator included in the pump driving circuit.

As roughly shown in FIG. 6A, the step-up regulator 62 has an inductor 72 and a diode 73 that are connected in series between an input terminal 71 and an output terminal 76, a switching element (in this example, a MOSFET; Metal-Semiconductor-Oxide Field Effect Transistor) 74 that is connected between the contact point between the inductor 72 and the diode 73 and the grounding potential, and an step-up control unit 75.

The input terminal 71 of the step-up regulator 62 receives the first DC voltage V1 (3 V in this example) from the power supply unit (battery) 53. Also, due to the switching element 74 being switched on and off according to a control signal CG from the step-up control unit 75, the first DC voltage V1 is stepped up and output to the output terminal 76 as a second DC voltage V2. The second DC voltage V2 is returned to the step-up control unit 75 as a feedback signal FB. Based on the feedback signal FB, the switching element 74 is switched on and off using the control signal CG of the step-up control unit 75 such that the second DC voltage V2 is a target value. The target value for the second DC voltage V2 is set using a step-up control signal CTL1 from the CPU 100 shown in FIG. 5.

Specifically, the step-up control signal CTL1 from the CPU 100 is a PWM signal, and according to the pulse width of the PWM signal, the step-up regulator 62 variably controls the second DC voltage V2 at the target value and outputs it. Accordingly, the second DC voltage V2 can be finely varied (stepped up or stepped down) in units of 0.1 V.

Figure 6B:
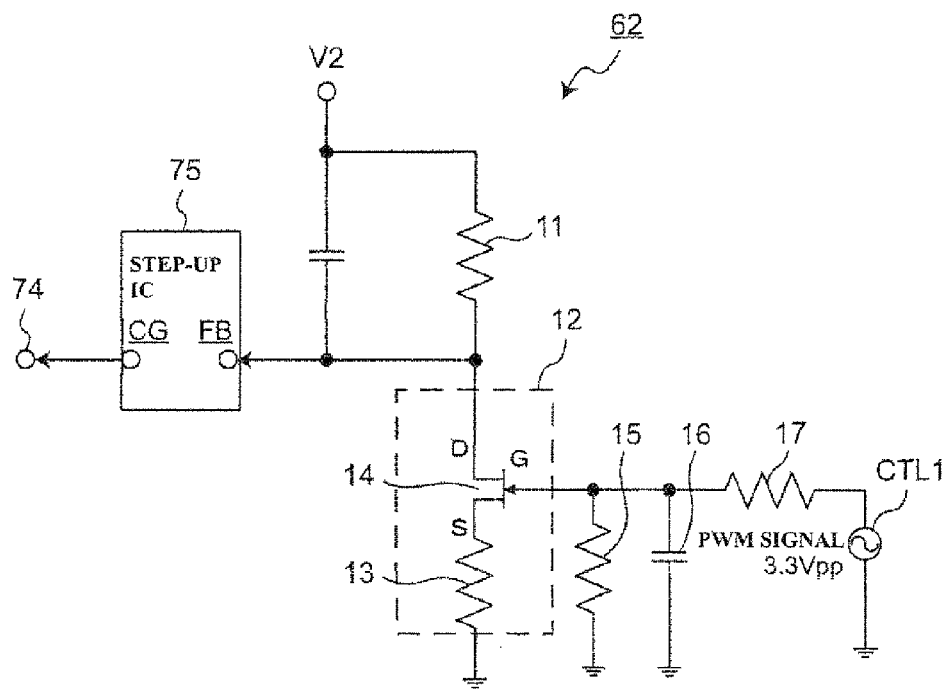
FIG. 6B is a partially detailed view showing a block configuration of the step-up regulator included in the pump driving circuit.

The configuration from the second DC voltage V2 in FIG. 6A to the terminal that receives input of the feedback signal FB of the step-up control unit (step-up IC) 75 will be described in detail with reference to FIG. 6B. The step-up regulator 62 has a fixed resistor 11 that has one end connected to the feedback signal FB, a FET 14 whose gate receives input of the step-up control signal CTL1, and whose drain is connected in series to the other end of the fixed resistor 11, a resistor 13 that has one end that is connected in series to the source of the FET 14 and another end that is grounded, a resistor 15 that has one end that is connected in parallel with a path between the step-up control signal CTL1 generation unit and the gate of the FET 14, and another end that is grounded, a capacitor 16 that is connected similarly to the resistor 15, and a resistor 17 that is connected in series to the path between the step-up control signal CTL1 generation unit and the gate of the FET 14. Here, the fixed resistor 11 corresponds to the "second resistance unit" in the claims, and a variable resistance unit 12 that includes the FET 14 and the resistor 13 corresponds to the "first resistance unit" in the claims.

The step-up control signal CTL1 is a PWM signal that is output from the CPU, for example, and has a square waveform with a normal duty ratio of 50%. The output level of the step-up control signal CTL1 is adjusted by dividing the voltage between the resistor 15 and the resistor 17, and the signal is smoothed using the resistor 15 and the capacitor 16.

Next, the smoothed voltage (DC voltage) is input to the gate of the FET 14. Here, the level of the smoothed voltage (DC voltage) is increased or reduced by increasing or reducing the duty ratio of the step-up control signal CTL1, and therefore it is possible to increase or reduce the resistance value of the variable resistance unit 12 (the equivalent resistance value that is derived from the impedance of the FET 14).

The voltage of the feedback signal FB that is applied to the step-up IC 75 is determined as a voltage obtained by dividing the second DC voltage V2 according to the divided voltage ratio between the fixed resistor 11 and the variable resistance unit 12 (resistance value of fixed resistor 11/ (resistance value of fixed resistor 11+resistance value of variable resistance unit 12)). By causing the voltage to be fed back to the step-up IC 75, it is possible to variably output the second DC voltage corresponding to the divided voltage ratio.

By doing so, the driving voltage of the pump can be adjusted easily. Also, it is possible to cause the pump to operate stably such that an appropriate pressure is output.

Figure 7:
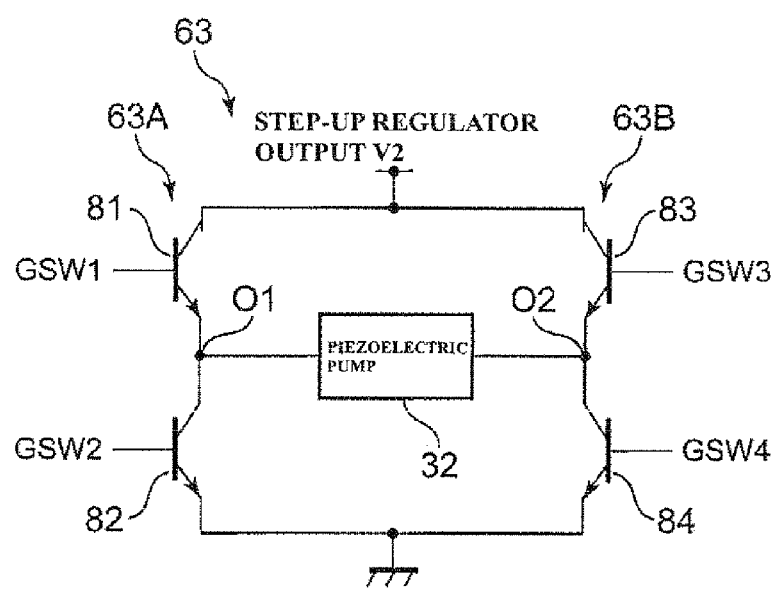
FIG. 7 is a diagram showing a block configuration of an H-bridge circuit included in the pump driving circuit.

As shown in FIG. 7, the H bridge circuit 63 has a first series circuit 63A that includes two switching elements (in this example, NPN bipolar transistors) 81 and 82 that are connected in a series between a high potential (potential V2) corresponding to the second DC voltage V2 output by the step-up regulator 62 and a grounding potential (zero potential) serving as a reference potential that is lower than the high potential. Also, a second series circuit 63B that includes two switching elements (in this example, NPN bipolar transistors) 83 and 84 connected in series is similarly included between the high potential V2 corresponding to the second DC voltage V2 and the grounding potential (zero potential). The switching elements 81, 82, 83, and 84 are switched on when bridge control signals GSW1, GSW2, GSW3, and GSW4 are at the H (high) level, and are switched off when the bridge control signals GSW1, GSW2, GSW3, and GSW4 are at the L (low) level.

The two switching elements 81 and 82 of the first series circuit 63A and the two switching elements 83 and 84 of the second series circuit 63B are switched on or off by the bridge control signals GSW1, GSW2, GSW3, and GSW4 (indicated as a whole by "CTL2" in FIG. 5) from the CPU 100, as will be described in detail later. As a result, a voltage (Vout) that is generated between a first contact point O1 between the two switching elements 81 and 82 of the first series circuit 63A and a second contact point O2 between the two switching elements 83 and 84 of the second series circuit 63B is used as a driving voltage for driving the pump 32.

Also, the bridge control signals GSW1, GSW2, GSW3, and GSW4 output by the CPU 100 make it possible to finely control the switching on and off using a PWM (Pulse Width Modulation) signal and to finely control the driving frequency for the pump in units of 100 Hz, for example.

As can be understood from the description above, the pump 32, the pump driving circuit 320, and the CPU 100 serving as a control unit constitute a pump driving system.

Note that in the upper portion of FIG. 5, the waveforms of the first DC voltage V1 from the power supply unit (battery) 53, the second DC voltage V2 output by the step-up regulator 62, and the driving voltage (voltage between terminals O1 and O2) that is applied to the pump 32 are represented schematically to facilitate understanding.

FIG. 9 specifically shows the most basic operation waveforms as an example of the waveforms of the driving voltage (voltage between terminals O1 and O2) Vout that is applied to the pump 32, and the bridge control signals GSW1, GSW2, GSW3, and GSW4 with respect to the switching elements 81, 82, 83, and 84 from the CPU 100. FIGS. 9A to 9D show that the levels of the bridge control signals GSW1, GSW2, GSW3, and GSW4 transition between the H level and the L level as time t elapses, and 9E shows that the voltage Vout between terminals O1 and O2 changes along with the changes in the levels of the bridge control signals GSW1, GSW2, GSW3, and GSW4 (the same goes for FIGS. 10, 11, 12, and 13). Note that in this example, the period in which the O1 terminal reaches a higher potential than the O2 terminal is called "positive voltage application period", and the period in which the O1 terminal reaches a lower potential than the O2 terminal is called "negative voltage application period".

With the operation waveforms in FIG. 9, the two switching elements 81 and 82 of the first series circuit 63A are switched on and off in a complimentary manner, or in other words, alternatingly using square waveforms (FIGS. 9A and 9B). In addition, according to the square waveforms, the two switching elements 83 and 84 of the second series circuit 63B are switched on and off in a complimentary manner with a phase that is the inverse of that of the switching on and off of the two switching elements 81 and 82 of the first series circuit 63A (FIGS. 9C and 9D). Accordingly, the switching elements 81 and 84 are both in the on state and the off state at the same times, and the switching elements 82 and 83 are in the on state and the off state at the same times, with a phase that is the inverse of that of the switching elements 81 and 84.

As a result, as shown in FIG. 9E, when V2 (>0) is used as the second DC voltage output by the step-up regulator 62, the waveforms of the driving voltage (voltage between terminals O1 and O2) Vout that are applied to the pump 32 are periodically repeated alternatingly between the positive voltage application period T1, during which +V2 is applied, and the negative voltage application period T2, during which −V2 is applied. The repetition cycle of the positive voltage application period T1 and the negative voltage application period T2 is made to coincide with the oscillation cycle T of the piezoelectric pump (or more accurately, the piezoelectric element) serving as the pump 32. Note that in this example, the resonance frequency of the piezoelectric pump is around 100 kHz, and as a result, the resonance cycle T is around 10 microseconds.

According to this, an AC voltage whose frequency matches the resonance cycle T is applied as the driving voltage Vout to the piezoelectric pump serving as the pump 32. Accordingly, the piezoelectric pump can operate so as to send air to the fluid bladder 22 of the cuff 20.

In such a case, in order to obtain a driving voltage having an amplitude of around 50 Vp-p (peak-to-peak voltage), for example, so as to drive the piezoelectric pump, it is sufficient that the step-up regulator 62 outputs a voltage that is half of the amplitude needed for the driving voltage, or in other words, a maximum of 25 V as the second DC voltage V2. Accordingly, the power supply can be configured by a 3-V dry-cell battery (1.5 V×2), for example. Also, the step-up regulator 62 can be configured to have a smaller size and a lower cost. Furthermore, the H bridge circuit 63 itself can also be configured to have a smaller size and a lower cost due to the fact that there are relatively few parts.

Also, in order to switch the two switching elements 81 and 82 of the first series circuit 63A and the two switching elements 83 and 84 of the second series circuit 63B on and off, the CPU 100 need only output four digital signals as the bridge control signals GSW1, GSW2, GSW3, and GSW4, and therefore the load is small. Accordingly, the CPU 100 can be constituted by an existing CPU (Central Processing Unit) that is included in the blood pressure meter 1, for example, without providing a special new part. Also, the bridge control signals GSW1, GSW2, GSW3, and GSW4 output by the CPU 100 make it possible to finely control the switching on and off as described above, and to finely control the driving frequency for the pump 32 in units of 100 Hz, for example. Accordingly, variation in the properties of the piezoelectric pump (in particular, variation in the resonance frequency), for example, can be easily adapted to.

Also, as described above, the step-up regulator 62 can finely step up the second DC voltage V2 in units of 0.1 V, for example, according to the step-up control signal CTL1 output by the CPU 100. Accordingly, inflation at a constant speed (e.g., 10 mmHg/sec) can be performed easily according to the piezoelectric pump serving as the pump 32, for example.

Accordingly, with the blood pressure meter 1, it is possible to achieve a smaller size, a lower cost, and improved performance.

FIG. 10 shows another example of waveforms of the bridge control signal GSW1, GSW2, GSW3, and GSW4 with respect to the switching elements 81, 82, 83, and 84 and the driving voltage (voltage between terminals O1 and O2) Vout applied to the pump 32, from the CPU 100.

The operation waveforms in FIG. 10 differ from the operation waveforms in FIG. 9 in that a resting period tdd in which all switching elements are off is provided between the on period of a switching element and a subsequent on period of another switching element.

Specifically, as shown in FIGS. 10A to 10D, compared to the operation waveforms in FIG. 9, the time at which the bridge control signals GSW1 and GSW4 transition from the H level to the L level is earlier by tdd, and as a result, the time at which the switching elements 81 and 84 transition from the on state to the off state is earlier by tdd. Similarly, the time at which the bridge control signals GSW2 and GSW3 transition from the H level to the L level is earlier by tdd, and as a result, the time at which the switching elements 82 and 83 transition from the on state to the off state is earlier by tdd.

Accordingly, as shown in FIG. 10E, between the positive voltage application period T1 and the negative voltage application period T2, a period of zero applied voltage (tdd) appears in the waveform of the driving voltage (voltage between terminals O1 and O2) Vout that is applied to the pump 32.

As a result, when the driving voltage Vout is reversed, or in other words, when the positive voltage application period T1 is started, or when the negative voltage application period T2 is started, inrush currents to the piezoelectric pump serving as the pump 32 are restricted. Accordingly, power consumption at the time of reversing the driving voltage Vout is suppressed, and energy conservation is realized.

FIG. 11 shows yet another example of waveforms of the bridge control signals GSW1, GSW2, GSW3, and GSW4 with respect to the switching elements 81, 82, 83, and 84 and the driving voltage (voltage between terminals O1 and O2) Vout applied to the pump 32, from the CPU 100.

The operation waveforms in FIG. 11 differ from the operation waveforms in FIG. 9 in that the switching elements 81, 82, 83, and 84 are caused to transition from the off state to the on state and from the on state to the off state in finite transition periods.

Figure 8:
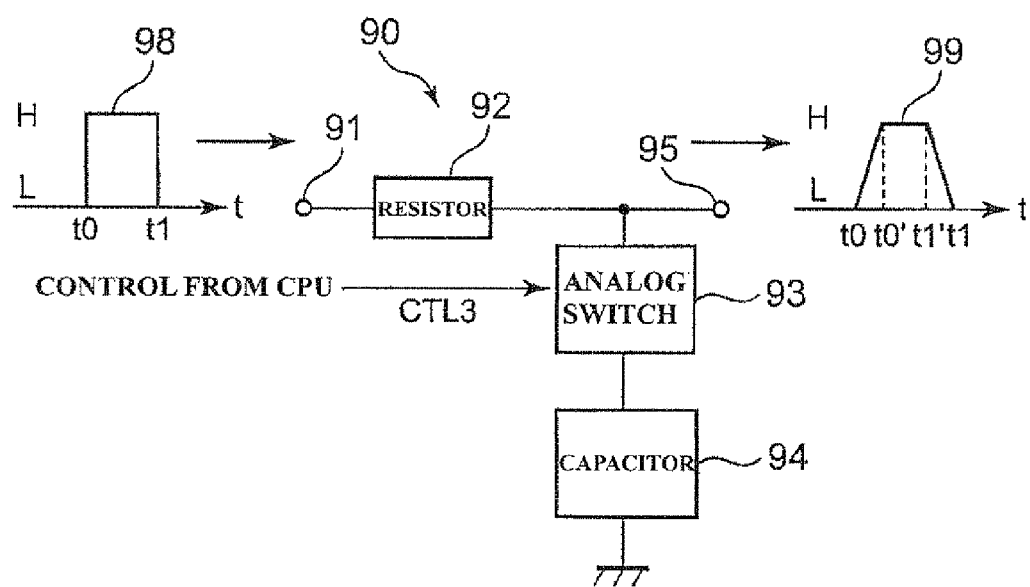
FIG. 8 is a diagram showing a configuration of a circuit for causing the switching elements of the H bridge circuit to transition from an off state to an on state, and from the on state to the off state in finite transition periods.

Specifically, a filter circuit 90 as shown in FIG. 8 is provided between the CPU 100 and the H bridge circuit 63. The filter circuit 90 has a resistor 92 that is provided between the input terminal 91 on the CPU 100 side, and the output terminal 95 on the H bridge circuit 63 side, and an analog switch 93 and a capacitor 94 that are connected in series between the output terminal 95 and the grounding potential. The analog switch 93 is switched on and off by the transition control signal CTL3 from the CPU 100 and indicates a finite on resistance in the on state.

When the square waveform 98 formed by the bridge control signals GSW1, GSW2, GSW3, and GSW4 from the CPU 100 are input to the terminal 91, the capacitor 94 is charged through the finite on resistance of the analog switch 93. As a result, a trapezoidal waveform 99 is output from the output terminal 95. The waveform 99 transitions from the L level to the H level over a finite transition period (t0 to t0') and transitions from the H level to the L level over a finite transition period (t1' to t1).

As shown in FIGS. 11A to 11D, the bridge control signals GSW1, GSW2, GSW3, and GSW4 from the CPU 100 all have the above-described trapezoidal waveform 99.

Accordingly, as shown in FIG. 11E, the waveform of the driving voltage (voltage between terminals O1 and O2) Vout that is applied to the pump 32 also has a trapezoidal waveform in the positive voltage application period T1 and the negative voltage application period T2. That is to say, when the positive voltage application period T1 is started, the driving voltage Vout transitions from zero to +V2 over a finite transition period (t0 to t0'), and when the positive voltage application period T1 ends, the driving voltage Vout transitions from +V2 to zero over a finite transition period OF to t1). Similarly, when the negative voltage application period T2 is started, the driving voltage Vout transitions from zero to −V2 over a finite transition period t0 to t0', and when the negative voltage application period T2 ends, it transitions from −V2 to zero over a finite transition period t1' to t1.

As a result, when the driving voltage Vout is reversed, or in other words, when the positive voltage application period T1 is started, or when the negative voltage application period T2 is started, inrush currents to the piezoelectric pump serving as the pump 32 are restricted. Accordingly, power consumption at the time of reversing the driving voltage Vout is suppressed, and energy conservation is realized.

FIG. 12 shows yet another example of waveforms of the bridge control signals GSW1, GSW2, GSW3, and GSW4 with respect to the switching elements 81, 82, 83, and 84 and the driving voltage (voltage between terminals O1 and O2) Vout applied to the pump 32, from the CPU 100.

The operation waveform in FIG. 12 is a combination of the operation waveform in FIG. 10 and the operation waveform in FIG. 11. That is to say, as shown in FIGS. 12A to 12D, similarly to the operation waveforms in FIG. 10, a resting period tdd in which all switching elements are off is provided between the on period of a switching element and a subsequent on period of another switching element. Moreover, similarly to the operation waveforms of FIG. 11, the switching elements 81, 82, 83, and 84 are caused to transition from the off state to the on state and from the on state to the off state in finite transition periods.

Accordingly, as shown in FIG. 12E, a period of zero applied voltage (tdd) appears in the waveform of the driving voltage (voltage between terminals O1 and O2) Vout that is applied to the pump 32 between the positive voltage application period T1 and the negative voltage application period T2. Moreover, the waveforms of the driving voltage (voltage between terminals O1 and O2) Vout applied to the pump 32 are trapezoidal waveforms in the positive voltage application period T1 and the negative voltage application period T2.

As a result, when the driving voltage Vout is reversed, or in other words, when the positive voltage application period T1 is started, or when the negative voltage application period T2 is started, inrush currents to the piezoelectric pump serving as the pump 32 are further restricted. Accordingly, power consumption at the time of reversing the driving voltage Vout is further suppressed, and energy conservation is realized.

FIG. 13 shows operation waveforms in the case of using a DC motor driven rotary pump instead of a piezoelectric pump as the pump 32.

With the operation waveforms of FIG. 13, among the two switching elements 81 and 82 of the first series circuit 63A, the switching element 81 on the high potential side is switched on and off by a rectangular waveform, and the switching element 82 on the grounding potential side is kept in the off state (FIGS. 13A and 13B). In addition, among the two switching elements 83 and 84 of the second series circuit 63B, the switching element 83 on the high potential side is kept in the off state, and the switching element 84 on the grounding potential side is switched on and off using a rectangular waveform with a phase that is the inverser of that of the switching on and off of the switching element 81 on the high potential side of the first series circuit 63A (FIGS. 13C and 13D).

As a result, as shown in FIG. 13E, when V2 (>0) is used as the second DC voltage that is output by the step-up regulator 62, the waveforms of the driving voltage (voltage between terminals O1 and O2) Vout applied to the pump 32 are alternatingly repeated periodically in a positive voltage application period Δt1 during which +V2 is applied, and a period Δt2 during which zero voltage is applied.

According to this, a periodic positive voltage is applied as the driving voltage Vout to the DC motor driven rotary pump serving as the pump 32. Accordingly, the motor driven rotary pump can operate so as to send air to the fluid bladder 22 of the cuff 20.

The driving of the pump 32 that is constituted by the DC motor driven rotary pump is controlled by fixing the second DC voltage V2 and varying the duty ratio Δt1/(Δt1+Δt2).

As described above, with the blood pressure meter and pump driving system of the embodiment, it is possible to achieve a smaller size, a lower cost, and improved performance. In particular, attention is given to the fact that the power supply can be constituted by a 3-V dry battery (1.5 V×2), and that the size V2 and frequency of the driving voltage Vout of the pump 32 can easily be controlled by the CPU 100. Furthermore, attention is given to the fact that driving can be performed using a piezoelectric pump or a rotary pump as the pump 32.

Note that the above embodiment is merely an example, and various modifications are possible without straying from the gist of the invention.

REFERENCE SIGNS LIST

1 Blood pressure meter
20 Blood pressure measurement cuff
62 Step-up regulator
63 H bridge circuit
100 CPU
320 Pump driving circuit

The invention claimed is:

1. A blood pressure meter, comprising:
a piezoelectric pump configured to send a fluid to a blood pressure measurement cuff;
a pump driving circuit for driving the piezoelectric pump; and
a processor configured to control the pump driving circuit in order to measure blood pressure, wherein
the pump driving circuit includes:
 a step-up unit that steps up a first DC voltage from a power supply and outputs it as a second DC voltage according to a step-up control signal from the processor, and
 an H bridge unit including first and second series circuits that each include two switching elements that are connected in series between a high potential corresponding to the second DC voltage and a reference potential that is lower than the high potential, the two switching elements of the first series circuit are switched on and off in a complementary manner according to bridge control signals from the processor, and the two switching elements of the second series circuit are switched on and off in a complementary manner with a phase that is an inverse of that of the switching on and off of the two switching elements of the first series circuit, a voltage that is generated between a first contact point between the two switching elements of the first series circuit and a second contact point between the two switching elements of the second series circuit is used as a driving voltage for driving the piezoelectric pump, and the processor is configured to set a rest period in which all switching elements are off between an on period of a switching element in each of the first and second series circuits and an on period of another switching element that follows the on period.

2. The blood pressure meter according to claim 1, wherein the step-up unit is a step-up regulator that varies and outputs the second DC voltage according to the step-up control signal from the processor.

3. The blood pressure meter according to claim 2, wherein the step-up control signal from the processor is a pulse width modulation signal, and the step-up regulator serving as the step-up unit varies and outputs the second DC voltage according to the pulse width of the pulse width modulation signal.

4. A blood pressure meter, comprising:

a piezoelectric pump configured to send a fluid to a blood pressure measurement cuff;

a pump driving circuit for driving the piezoelectric pump; and a processor configured to control the pump driving circuit in order to measure blood pressure, wherein the pump driving circuit includes:
 a step-up unit that steps up a first DC voltage from a power supply and outputs it as a second DC voltage according to a step-up control signal from the processor, and
 an H bridge unit including first and second series circuits that each include two switching elements that are connected in series between a high potential corresponding to the second DC voltage and a reference potential that is lower than the high potential, the two switching elements of the first series circuit are switched on and off in a complementary manner according to bridge control signals from the processor, and the two switching elements of the second series circuit are switched on and off in a complementary manner with a phase that is an inverse of that of the switching on and off of the two switching elements of the first series circuit, a voltage that is generated between a first contact point between the two switching elements of the first series circuit and a second contact point between the two switching elements of the second series circuit is used as a driving voltage for driving the piezoelectric pump, and the processor is configured to cause the switching elements of the first and second series circuits to transition from an off state to an on state and from the on state to the off state over finite transition periods.

5. The blood pressure meter according to claim 4, wherein the step-up unit is a step-up regulator that varies and outputs the second DC voltage according to the step-up control signal from the processor.

6. The blood pressure meter according to claim 5, wherein the step-up control signal from the processor is a pulse width modulation signal, and the step-up regulator serving as the step-up unit varies and outputs the second DC voltage according to the pulse width of the pulse width modulation signal.

7. A pump driving system, comprising:

a piezoelectric pump;

a pump driving circuit for driving the piezoelectric pump; and a processor configured to control the pump driving circuit, wherein the pump driving circuit includes:
 a step-up unit that steps up a first DC voltage from a power supply and outputs it as a second DC voltage according to a step-up control signal from the processor, and
 an H bridge unit including first and second series circuits that each include two switching elements that are connected in series between a high potential corresponding to the second DC voltage and a reference potential that is lower than the high potential, the step-up control signal from the processor is a pulse width modulation signal, the step-up unit is a step-up regulator that includes a first resistance unit that includes a resistor and a FET and varies the resistance value according to the pulse width of the pulse width modulation signal, and a second resistance unit, and can vary and output the second DC voltage by dividing the second DC voltage between the first resistance unit and the second resistance unit and causing it to be fed back, the two switching elements of the first series circuit are switched on and off in a complementary manner according to bridge control signals from the processor, and the two switching elements of the second series circuit are switched on and off in a complementary manner with a phase that is an inverse of that of the switching on and off of the two switching elements of the first series circuit, a voltage that is generated between a first contact point between the two switching elements of the first series circuit and a second contact point between the two switching elements of the second series circuit is used as a driving voltage for driving the piezoelectric pump, and the processor configured to set a rest period in which all switching elements are off between an on period of a switching element in each of the first and second series circuits and an on period of another switching element that follows the on period.

8. The pump driving system according to claim 7, wherein:

the processor is configured to cause the switching elements of the first and second series circuits to transition from an off state to an on state and from the on state to the off state over finite transition periods.

* * * * *